United States Patent
Fujieda

(10) Patent No.: US 6,655,805 B2
(45) Date of Patent: Dec. 2, 2003

(54) OPHTHALMIC APPARATUS

(75) Inventor: Masanao Fujieda, Toyohashi (JP)

(73) Assignee: Nidek Co., Ltd., Gamagori (JP)

( * ) Notice: Subject to any disclaimer, the term of this patent is extended or adjusted under 35 U.S.C. 154(b) by 100 days.

(21) Appl. No.: 09/817,272

(22) Filed: Mar. 27, 2001

(65) Prior Publication Data

US 2001/0024265 A1 Sep. 27, 2001

(30) Foreign Application Priority Data

Mar. 27, 2000 (JP) .......................................... 2000-086475

(51) Int. Cl.$^7$ ................................................. A61B 3/10
(52) U.S. Cl. ........................................................ 351/212
(58) Field of Search ................................ 351/204, 205, 351/208, 209, 210, 211, 212, 246; 606/4, 5

(56) References Cited

U.S. PATENT DOCUMENTS

| 5,557,350 A | 9/1996 | Yano |
| 5,696,573 A | * 12/1997 | Miwa .......................... 351/208 |
| 5,889,576 A | 3/1999 | Fujieda |

* cited by examiner

*Primary Examiner*—George Manuel
(74) *Attorney, Agent, or Firm*—Finnegan, Henderson, Farabow, Garrett & Dunner, LLP

(57) ABSTRACT

An ophthalmic apparatus comprising a first input unit with which plural measurement data concerning an eye to be examined are inputted, a second input unit with which images of the eye including an anterior eye segment are inputted, each of the image is photographed at the time of measuring each of the inputted measurement data, and a calculation and control unit which detects and corrects two-dimensional displacement or deviation between each of the measurement data based on each of the inputted images of the eye.

15 Claims, 6 Drawing Sheets

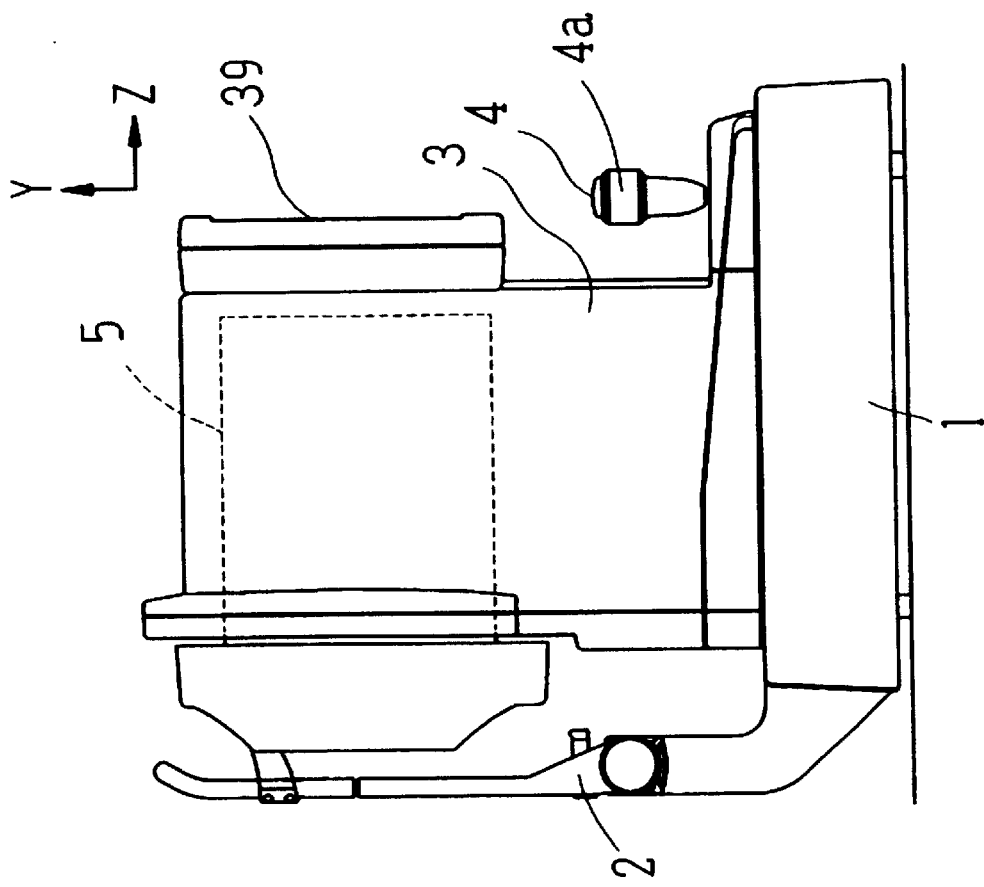
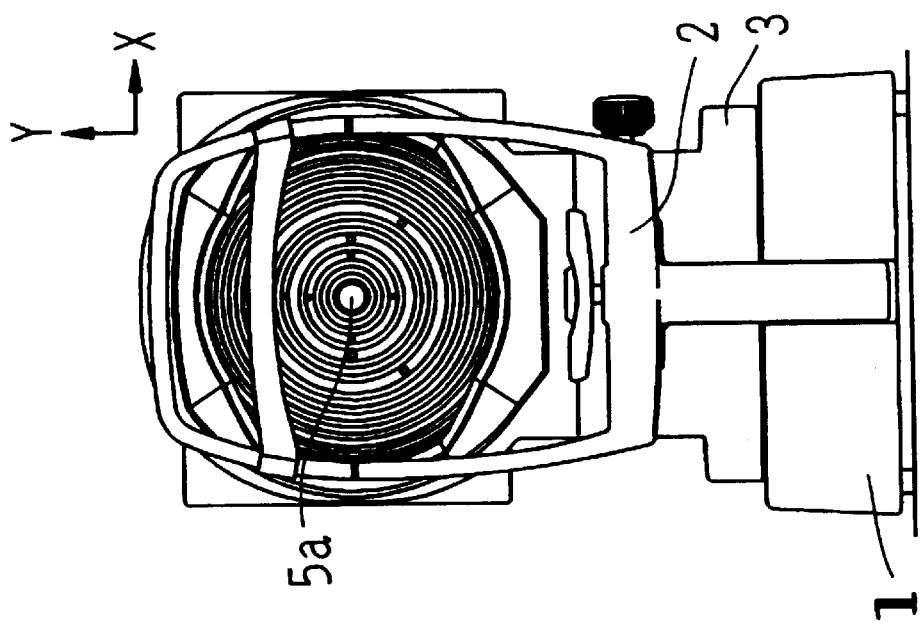
FIG. 1B
FIG. 1A

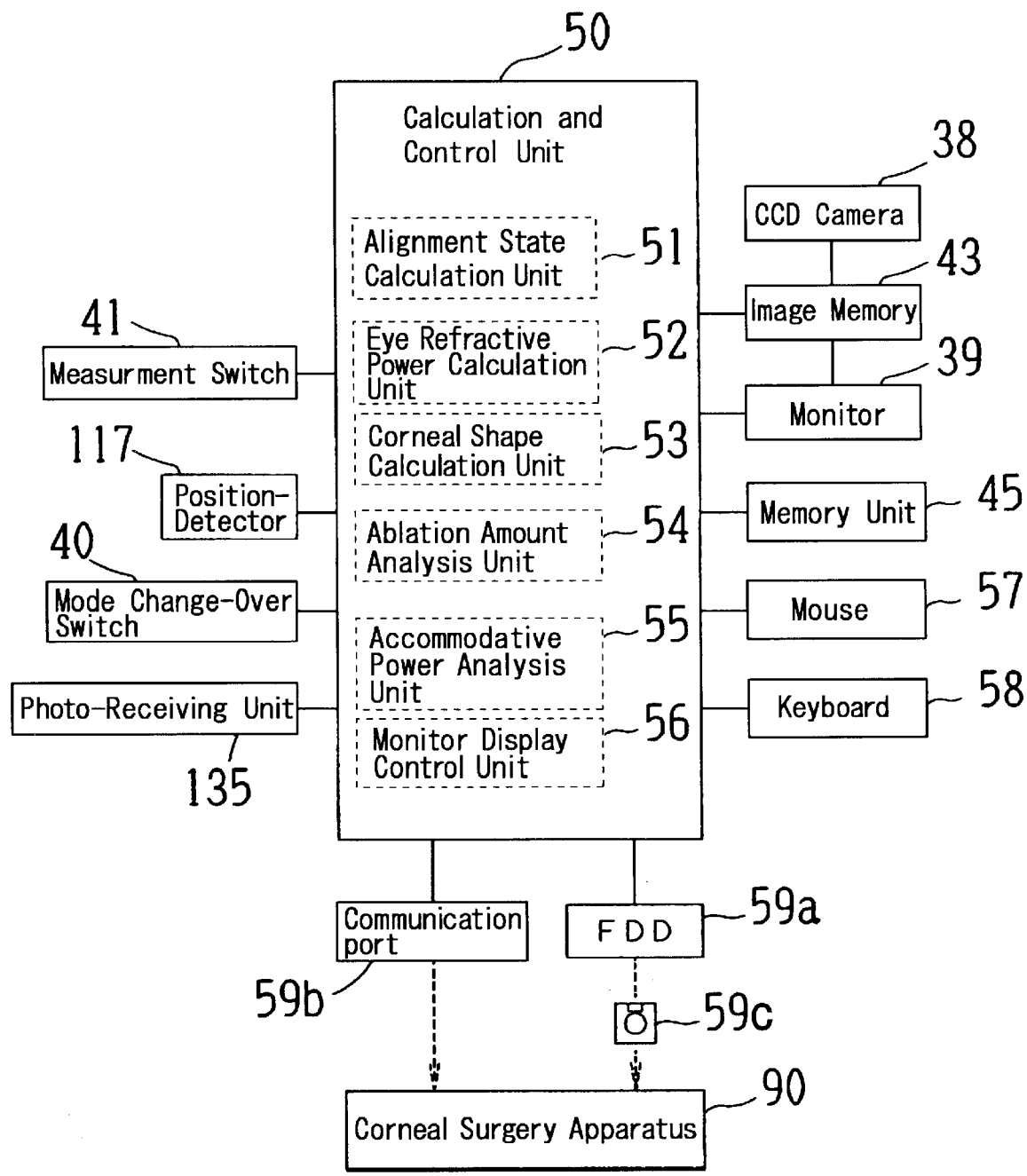
F I G. 3

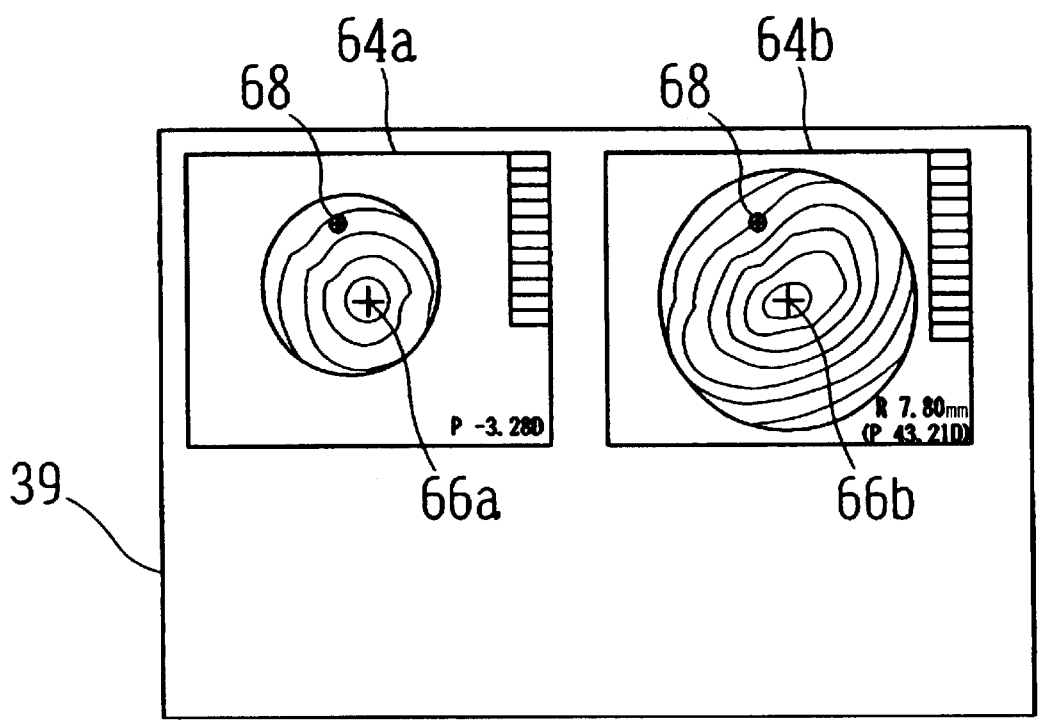
F I G. 8
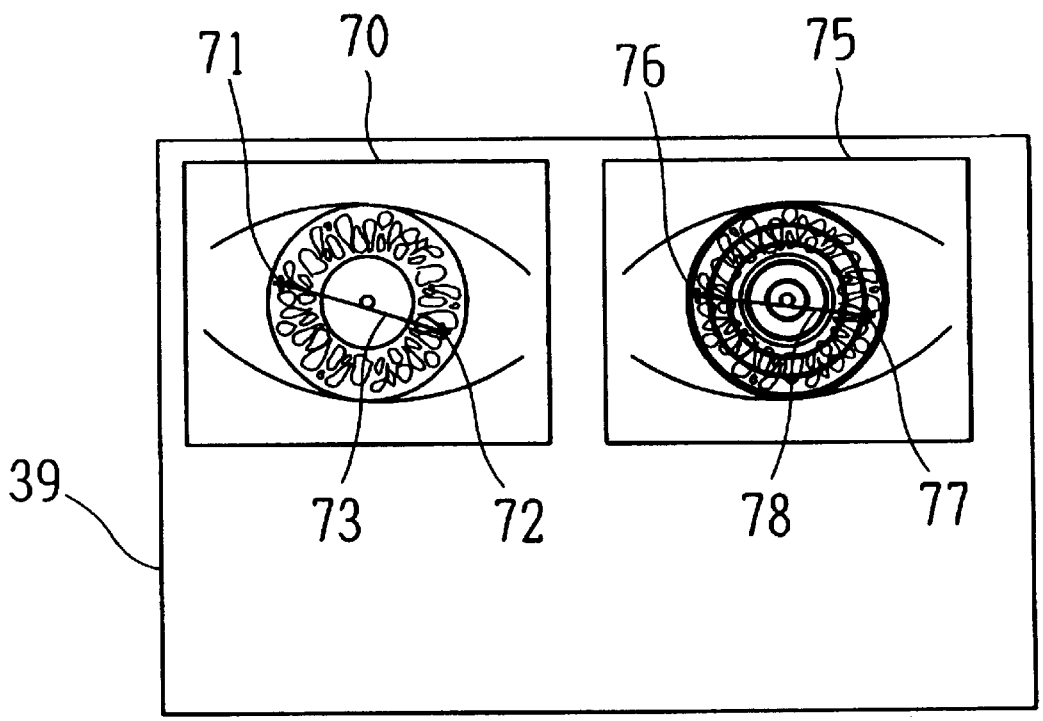
F I G. 9

OPHTHALMIC APPARATUS

BACKGROUND OF THE INVENTION

1. Field of the Invention

The present invention relates to an ophthalmic apparatus used by ophthalmologists or opticians.

2. Description of Related Art

As a known ophthalmic apparatus, there is an apparatus for obtaining distribution of corneal radius of curvature covering a wide area of a cornea using an image of placido rings formed on the cornea of the eye in order to visualize corneal topography. Also, there is an apparatus suggested, for example, in U.S. Pat. No. 5,907,388, for obtaining distribution of eye refractive power at a number of portions of the eye. Further, an apparatus suggested, for example, in U.S. Pat. No. 6,033,075 obtains data on an amount of cornea to be ablated based on these thus obtained data on distribution, and use the data in corneal refractive surgery.

However, in the case where plural data measured at different times are used to obtain new data or to examine the relation between each measurement data, each measurement data needs to be consistent in their two-dimensional positional relationship. If not, accurate results may not be obtained, and comparisons between them may not be easy.

SUMMARY OF THE INVENTION

The present invention has been made in view of the above circumstances and has an object to overcome the above problems and to provide an ophthalmic apparatus capable of aligning the positional relationship of plural measurement data measured at different times with each other so that comparisons and analyses of each measurement data may be carried out easily and accurately.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, an ophthalmic apparatus comprising a first input unit with which plural measurement data concerning an eye to be examined are inputted, a second input unit with which images of the eye including an anterior eye segment are inputted, each of the image is photographed at the time of measuring each of the inputted measurement data, and a calculation and control unit which detects and corrects two-dimensional displacement or deviation between each of the measurement data based on each of the inputted images of the eye.

In another aspect of the present invention, an ophthalmic apparatus comprising a corneal shape measurement unit which measures distribution of corneal radius of curvature of an eye to be examined, an eye refractive power measurement unit which measures distribution of eye refractive power of the eye, an alignment unit which detects an alignment state of the ophthalmic apparatus relative to the eye, and a calculation and control unit which detects and corrects two-dimensional displacement or deviation between each of data on the measured distribution with reference to at least an image of the eye including an anterior eye segment photographed by either the first photographing element or the second photographing element at the time of each measurement. The corneal shape measurement unit has an optical system for projecting a first measurement target onto a cornea of the eye, and an optical system provided with a first photographing element for detecting an image of the first measurement target formed on the cornea. The eye refractive power measurement unit has an optical system for projecting a second measurement target onto a fundus of the eye, and an optical system for detecting an image of the second measurement target formed on the fundus. The alignment unit has an optical system for projecting an alignment target onto the cornea of the eye, and an optical system provided with a second photographing element for photographing an image of the alignment target formed on the cornea.

In yet another aspect of the present invention, an ophthalmic apparatus comprising a first input unit with which plural measurement data concerning an eye to be examined are inputted, a second input unit with which displacement or deviation of the eye relative to a predetermined reference position at the time of measuring each of the inputted measurement data is inputted, and a calculation and control unit which detects and corrects two-dimensional displacement or deviation between each of the measurement data with reference to each of the inputted displacement.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings, FIGS. 1A and 1B are external views showing construction of an ophthalmic apparatus in accordance with one preferred embodiment of the present invention;

FIG. 3 is a schematic block diagram showing a control system of the apparatus;

FIG. 8 is a view showing an example of a screen displaying distribution of corneal radius of curvature and distribution of eye refractive power in a form of color map; and FIG. 9 is a view illustrating a way to correct angular deviation between data on distribution of corneal radius of curvature and data on distribution of eye refractive power.

DETAILED DESCRIPTION OF THE PREFERRED EMBODIMENTS

A detailed description of one preferred embodiment of an ophthalmic apparatus embodying the present invention will now be given referring to the accompanying drawings.

Figure 2:
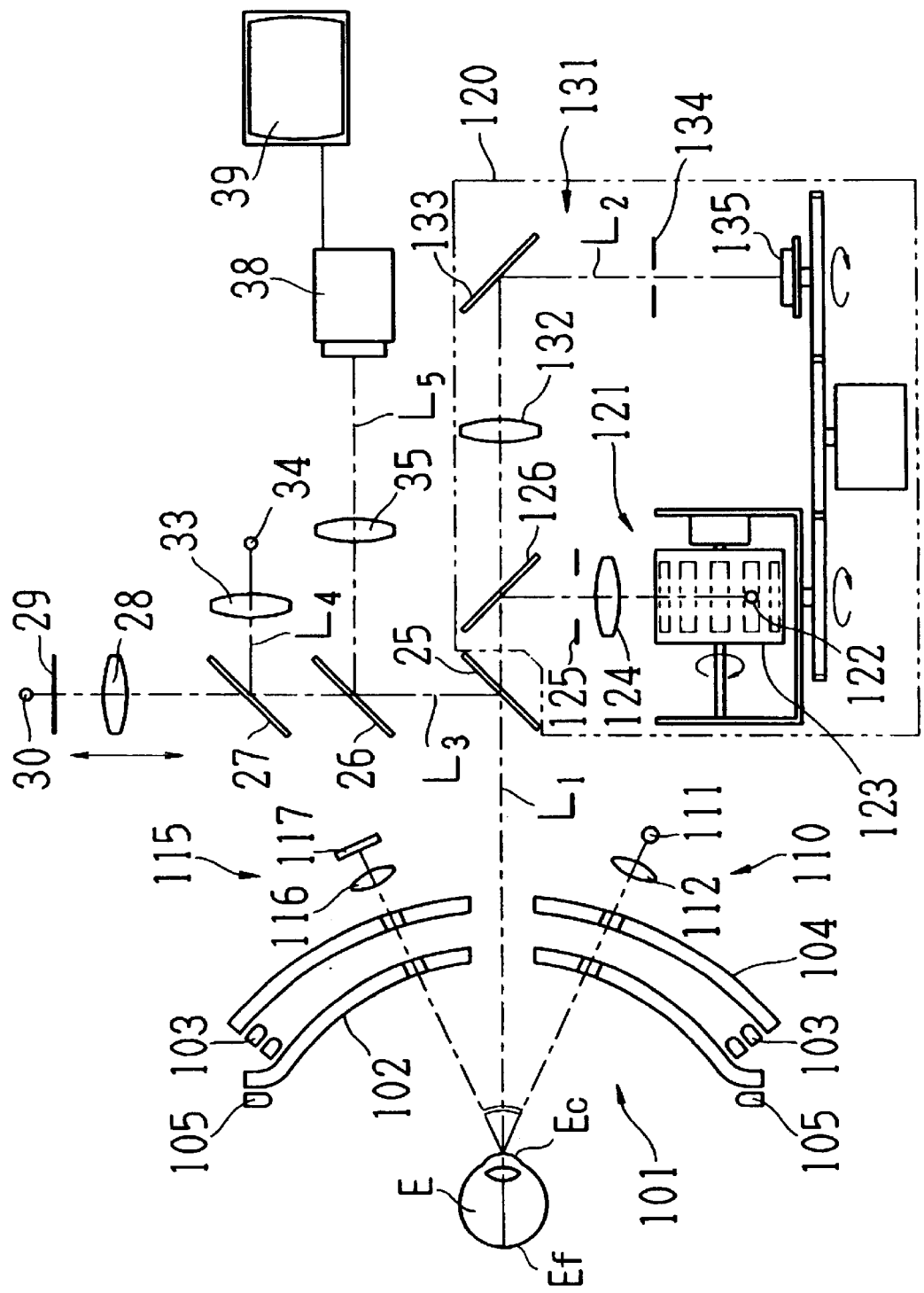
FIG. 2 is a schematic view showing construction of optical systems arranged inside a measurement unit of the apparatus.

FIGS. 1A and 1B are external views showing construction of the ophthalmic apparatus in accordance with the preferred embodiment of the present invention: FIG. 1A is a front view, looking from an examinee's side and FIG. 1B is a side view. FIG. 2 is a schematic view showing construction of optical systems arranged inside a measurement unit 5. FIG. 3 is a schematic block diagram showing a control system of the apparatus.

Reference numeral 1 denotes a fixed base. The base 1 has a head support unit 2 fixedly attached thereto for fixedly supporting an examinee's head. 5 is the measurement unit containing a measurement optical system, an alignment optical system and the like, which will be described later. The measurement unit 5 is provided with a measurement window 5a on a side facing to the examinee at an approximate center in the right-and-left direction (X direction) so that measurement light and the like can pass through. A main body 3 on which the measurement unit 5 is mounted slides along the base 1 in the right-and-left direction (X direction) and the back-and-forth direction (Z direction) by a known slide mechanism which works in response to operation of a joystick 4. In addition, the measurement unit 5 moves in the up-and-down direction (Y direction) relative to the main body 3 by a Y direction movement device comprising a motor and the like, which is driven via a calculation and control unit 50 in response to rotative operation of a rotation knob 4a mounted at the joystick 4. Further, to be ready for auto-alignment, the measurement unit 5 may be moved in the X, Y and Z directions relative to the main body 3 by the calculation and control unit 50 as well as an X direction movement device, the Y direction movement device and a Z direction movement device, each of which comprises a motor and the like.

Reference numeral 39 is a color monitor (display) for displaying various information to the examiner, such as an image of an eye to be examined, alignment information, measurement results and the like.

In FIG. 2, reference numeral 101 denotes a target projecting optical system for corneal shape measurement. 102 is a placido plate generally of a dome-shape having an opening at the center thereof, in which a ring pattern is formed with a number of concentric circles of light transmitting portions and light shielding portions with an optical axis L1 as the center. 103 are illumination light sources such as LEDs or the like, which emit red light, near infrared light, or infrared light. Light emitted from the light sources 103 is reflected by a reflecting plate 104 and illuminates the placido plate 102 approximately uniformly from behind so that an image of the ring pattern (an image of the placido rings) is formed on a cornea Ec of the eye E to be examined. On an outer circumference of the placido plate 102, anterior eye segment illumination light sources 105 which emit near infrared light are disposed.

Disposed behind the reflecting plate 104 are a target projecting optical system 110 for working distance detection and a target detecting optical system 115 for working distance detection: the former comprises a light source 111 such as an LED emitting near infrared light and a lens 112, and the latter comprises a lens 116 and a one-dimensional photo-detector (a position-detector) 117. Light emitted from the light source 111 is made generally parallel light by the lens 112 and passes through openings provided in the placido plate 102 and the reflecting plate 104 to illuminate the cornea Ec obliquely. As a result, the light source 111 forms a target image on the cornea Ec. Light of the target image formed on the cornea Ec passes though openings provided in the placido plate 102 and the reflecting plate 104 and then enters the detector 117 via the lens 116. Based on the incident position of the light on the detector 117, the calculation and control unit 50 detects an alignment state of the apparatus with the eye E in a working distance direction (Z direction).

An eye refractive power measurement optical system 120 is provided in a rear direction along the optical axis L1. The eye refractive power measurement optical system 120 comprises a slit light projecting optical system 121 and a slit image detecting optical system 131. Near infrared light emitted from a light source 122 included in the slit light projecting optical system 121 illuminates slit apertures provided to a rotation sector 123. The slit light scanned by rotation of the sector 123 passes through a projecting lens 124 and a limiting diaphragm 125, then is reflected by a beam splitter 126. Thereafter, the light passes through a beam splitter 25, then converges in a vicinity of the cornea Ec, and is projected onto a fundus Ef of the eye E.

Figure 4:
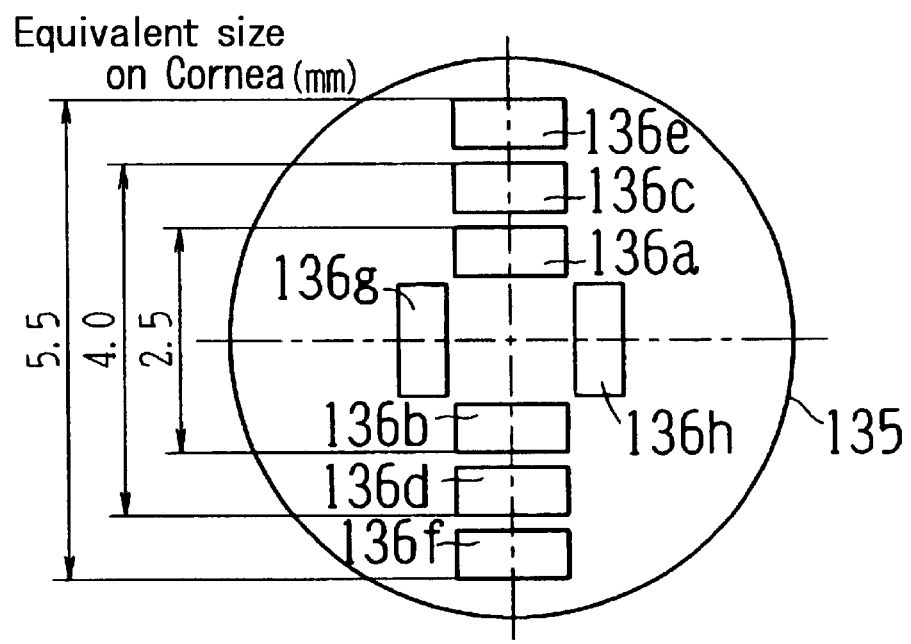
FIG. 4 is a view showing an arrangement of photo-detectors included in a photo-receiving unit of an eye refractive power measurement optical system.

The slit image detecting optical system 131 comprises a photo-receiving lens 132 and a mirror 133 both of which are disposed on an optical axis L1, as well as a diaphragm 134 and a photo-receiving unit 135 both of which are disposed on an optical axis L2 of light reflected by the mirror 133. The diaphragm 134 is arranged at a back focal point of the photo-receiving lens 132. The photo-receiving unit 135 has eight photo-detectors 136a–136h on its photo-receiving plane at generally conjugate positions with the cornea Ec relative to the photo-receiving lens 132 (see FIG. 4). Among the eight photo-detectors, the photo-detectors 136a–136f are located along a line passing though the center of the photo-receiving plane (the optical axis L2) such that the photo-detectors 136a and 136b, 136c and 136d, and 136e and 136f are symmetrical in relation to the center of the photo-receiving plane. These three pairs of photo-detectors are disposed at specific distances so as to be able to detect the refractive power at each corresponding portions of the cornea Ec in the meridian direction (In FIG. 4, the distances are shown in the equivalent size on the cornea Ec). On the other hand, the photo-detectors 136g and 136h are disposed on a line orthogonal to the photo-detectors 136a–136f to be symmetrical in relation to the optical axis L2.

This eye refractive power measurement optical system 120 is so configured that a rotation mechanism comprising a motor, a gear and the like rotates the sector 123 and the photo-receiving unit 135 respectively on their optical axes in synchronism.

Disposed on an optical axis L3, which is made coaxial with the optical axis L1 by the beam splitter 25 are a half mirrors 26 and 27, a lens 28, a fixation target plate 29, and an illumination light source 30 such as an LED which emits visible light. The fixation target plate 29 has a fixation point in the middle and an area surrounding the fixation point transmits visible light. The lens 28 is movable along the optical axis L3 so that the position of the fixation target plate 29 (fixation point) that the eye E gazes at is changed. This enables fogging the eye E or applying accommodative load to the eye E.

Disposed on an optical axis L4, which is made coaxial with the optical axis L3 by the half mirror 27 are a lens 33 and a light source 34 such as an LED which emits near infrared light. Light emitted from the light source 34 is made generally parallel light by the lens 33 and projected onto the cornea Ec from the front via the half mirrors 26 and 27, and the beam splitter 25. As a result, the light source 34 forms an image of an alignment target on the cornea Ec. Light of the target image formed on the cornea Ec enters a CCD camera 38 via the beam splitter 25, the half mirror 26 and a lens 35.

Disposed on an optical axis L5, which is made coaxial with the optical axis L3 by the half mirror 26 are the lens 35 and the CCD camera 38 serving as a photographing element. Output from the camera 38 is inputted into the monitor 39 directly or via the calculation and control unit 50. An image of an anterior eye segment of the eye E photographed by the camera 38 is displayed on the monitor 39. Also, an image of the placido rings and the target image by the light source 34 are subjected to image processing performed by the calculation and control unit 50, thereby to obtain the alignment state of the apparatus with the eye E in the up-and-down and the right-and-left directions (X and Y directions).

Now, description is given to operation of the apparatus. The present apparatus has functions of performing corneal shape measurement and eye refractive power measurement, so as to analyze each measurement data to obtain an amount of cornea to be ablated in refractive surgery. The apparatus also has functions of measuring distribution of eye refractive power under the condition where accommodation of the eye is relaxed (distribution of eye refractive power at far vision) and distribution of eye refractive power under the condition where accommodative load is applied to the eye (distribution of eye refractive power at near vision), so as to analyze accommodative power of the crystalline lens.

(I) Analysis of Amount of Cornea to be Ablated

First, description is given to corneal shape measurement. To start measurement, a corneal shape measurement mode is selected using a mode change-over switch 40. While observing the image of the anterior segment of the eye E illuminated by the illumination light sources 105 and displayed on the monitor 39, the examiner operates the joystick 4 and the like to align the apparatus (the measurement unit 5) with the eye E. To make alignment in the X and Y directions, an image of the alignment target, which is formed by the light source 34 at an optical center determined depending on the corneal optical system of the eye E (hereinafter, it is regarded to be the corneal center, which may be regarded also as an approximate center of the visual axis) is brought to the center of an aiming mark 60 displayed on the monitor 39 (see FIG. 5). This mark 60 may be generated electrically and its center is preliminarily adjusted to coincide with the photographing optical axis L5 of the camera 38 (the measurement optical axis L1). To make alignment in the Z direction, the calculation and control unit 50 displays an indicator for alignment on the monitor 39 based on information obtained by the detector 117 about deviation in the working distance direction. Then, the examiner moves the main body 3 in the Z direction according to the indicator.

After the alignment is done, at the push of a measurement switch 41, the light sources 103 are turned on for a predetermined period of time to form the image of the ring pattern on the cornea Ec. Then the image of the anterior eye segment is photographed by the camera 38 and stored in an image memory 43. A corneal shape calculation unit 53 conducts an image processing on the image stored in the memory 43 to detect edges of the image of the ring pattern. Then, by repeatedly detecting an edge position relative to the corneal center at every predetermined angle step (one degree), distribution of the corneal radius of curvature is obtained.

Further, at the push of the switch 41, an alignment state calculation unit 51 for determining an alignment state obtains information on alignment deviation in the X and Y directions relative to the optical axis L1 based on the image of the alignment target (the bright spot (reflex) formed on the cornea Ec by the light source 34) detected by the camera 38. The information on alignment deviation is stored in a memory unit 45 such as a hard disk together with the image of the anterior eye segment onto which the image of the ring pattern is formed, and the data on distribution of corneal radius of curvature. Here, to obtain information on alignment deviation at the time of corneal shape measurement, a center of the innermost image of the ring pattern may be detected and regarded as the corneal center.

In the case of eye refractive power measurement, an eye refractive power measurement mode is selected using the switch 40. Eye refractive power measurement is performed by directing measurement light into the eye E and receiving reflection light from the fundus Ef via the pupil. Generally, the corneal center and the pupillary center approximately coincide. Yet, there may be an eye with the pupillary center decentered largely. In such a case, if alignment in the X and Y directions is done with reference to the corneal center, measurement light is likely to be shaded by an iris. As a result, reflection light from the fundus Ef, which is necessary for the measurement, may not be detected so that possibility of measurement errors increases.

Figure 5:
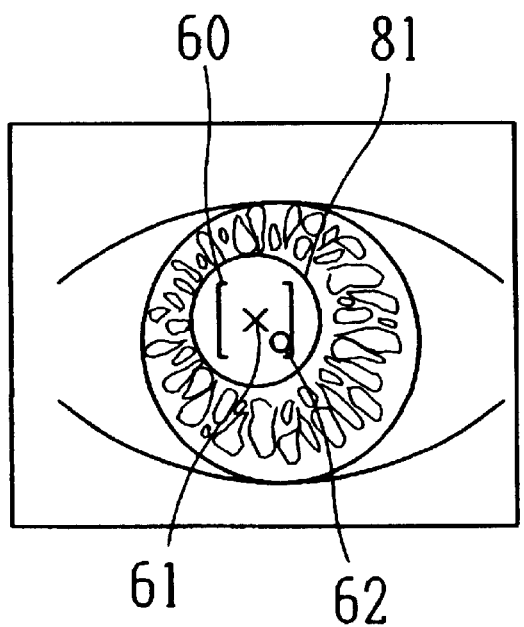
FIG. 5 is a view showing an alignment screen displayed in eye refractive power measurement.

In view of this undesirable possibility, the examiner observes the image of the anterior eye segment displayed on the monitor 39 to see if the pupillary center is decentered from the corneal center. If such is the case, alignment in the X and Y directions is performed with reference to the pupillary center. That is to say, as shown in FIG. 5, the alignment in the X and Y directions is performed to bring the center of the pupil 81 to the center of the mark 60 displayed on the monitor 39. Alignment in the Z direction is made preliminarily in accordance with the indicator displayed on the monitor 39.

After the alignment is adjusted, the examiner pushes the switch 41. At the push of the switch 41, the image of the anterior eye segment photographed by the camera 38 is stored in the memory 43 and eye refractive power measurement is performed. An eye refractive power calculation unit 52 obtains distribution of eye refractive power based on the phase difference of output signals from each photo-detector disposed in the photo-receiving unit 135. To meet this end, first, preliminary measurement is performed in the like manner as a conventional phase difference method to obtain refractive power. Based on the thus obtained result, the lens 28 is moved in order to fog the eye E. Thereafter, based on output signals from the photo-detectors 136$g$ and 136$h$ that vary in response to the movement of the slit image on the photo-receiving unit 135, the eye refractive power calculation unit 52 obtains the corneal center (or the center of the visual axis) in the meridian direction in which the photo-detectors 136$a$–136$f$ are disposed. Next, based on the phase difference of the output signals from each of the photo-detectors 136$a$–136$f$ with respect to the thus obtained center, refractive power at a plurality of corneal portions corresponding to each photo-detector is obtained. While rotating the sector 123 of the projecting optical system 121 and the photo-receiving unit 135 one hundred eighty degrees at a predetermined angle step (one degree) about the optical axes, refractive power along each meridian at every angle step is calculated. As a result, the distribution of eye refractive power which varies in the meridian direction is obtained (for the details, see U.S. Pat. No. 5,907,388).

Also at the push of the switch 41, the calculation unit 51 obtains information on alignment deviation in the X and Y directions relative to the optical axis L1 based on the image of the alignment target detected by the camera 38 similarly to the case of corneal shape measurement. The information on alignment deviation is stored in the memory unit 45 together with the image of the anterior eye segment and the data on distribution of eye refractive power.

Once each of the distribution data (measurement data), namely the data on the distribution of corneal radius of curvature and the data on eye refractive power distribution, are obtained on one and the same eye in the above manner, a keyboard 58 and a mouse 57 which are connected to the calculation and control unit 50 are operated following the instructions displayed on the monitor 39. Through the operations, each data on distribution and the information on alignment deviation are inputted to an ablation amount analysis unit 54 and a monitor display control unit 56 so that maps indicating each distribution data, calculation results of the corneal ablation amount and the like are displayed on the monitor 39.

Now, description is given to map-display of each distribution data. In the above-described eye refractive power measurement, as shown in FIG. 5, the case where the pupillary center is decentered from the corneal center is taken as an example so that the alignment is made in a manner to bring the center of the pupil 81 to the center of the mark 60. As a result, the image 62 of the alignment target formed on the corneal center comes to a position off the center 61 of the optical axis L1. On the contrary, at the time of corneal shape measurement, alignment is made in a manner to bring the target image 62 to the center of the mark 60. As a result, the target image 62 and the center 61 of the optical axis L1 coincide generally.

Figure 6:
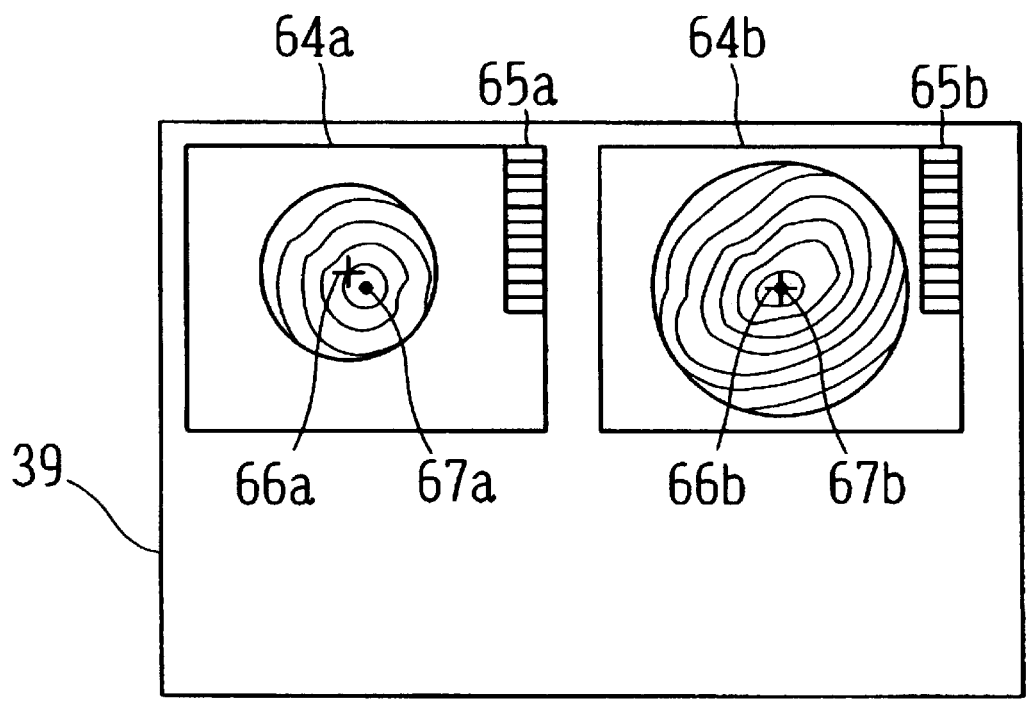
FIG. 6 is a view showing an example of a screen displaying distribution of corneal radius of curvature and distribution of eye refractive power in a form of color map consistent with a conventional technique.

In FIG. 6, the screen display is produced using a conventional color mapping technique. Two maps are tiled (displayed) on the same screen of the monitor 39: Displayed at the left area is a map 64a indicating distribution of eye refractive power, and at the right area is a map 64b indicating distribution of corneal radius of curvature. Black dots 67a and 67b each indicate the corneal center, and shown in the figure for the sake of convenience in explanation. In the maps 64a and 64b consistent with the conventional technique, the center of the measurement optical axis at the time of each measurement is made to coincide with marks 66a and 66b which indicate a displaying center of each area. In the case of making comparisons between the map 64a indicating distribution of eye refractive power and the map 64b indicating distribution of corneal radius of curvature displayed in this manner, it is difficult to see how a corneal portion shown in one map correspond to that in the other map in terms of their two-dimensional positions.

Figure 7:
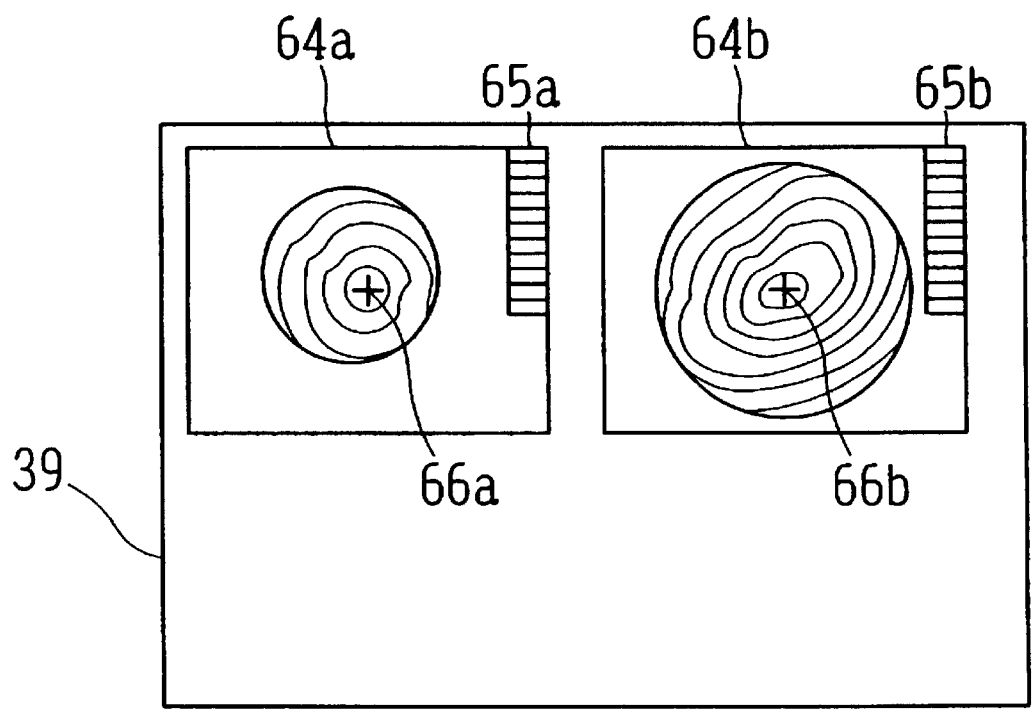
FIG. 7 is a view showing an example of a screen displaying distribution of corneal radius of curvature and distribution of eye refractive power in a form of color map.

In view of the above, as shown in FIG. 7, color maps in this preferred embodiment are displayed in the following manner. In each map, the corneal center obtained through detecting the image 62 of the alignment target is made to coincide with the center of the corresponding map, the mark 66a and 66b. In addition, the control unit 56 exerts control so as to display each map by a common reference. That is to say, in the case of the map 64a indicating distribution of eye refractive power, the map data is offset by an amount of alignment deviation so that the corneal center comes to the center of the mark 66a. These data on each distribution displayed in this manner are easy to compare their two-dimensional positions and easy to see. Reference numerals 65a and 65b in FIGS. 6 and 7 are color bars showing the color-coding of each map.

Further, since both the data on each distribution are aligned with each other, it is easy to find out measurement data at one portion of the cornea along with corresponding measurement data at the same portion of the cornea Ec. For example, as shown in FIG. 8, at a crick on an arbitrary point 68 on the map 64a or 64b with the mouse 57, both measurement values corresponding to that point are displayed simultaneously. That is, in the map 64a indicating the distribution of corneal refractive power, the refractive power corresponding to that point is displayed. Simultaneously, in the map 64b indicating the distribution of the corneal radius of curvature, the corneal radius of curvature corresponding to that point or the corneal refractive power converted from that corneal radius of curvature is displayed. At the time of producing such displays, if there is alignment deviation between the two maps, the displayed measurement values may not necessarily correspond to the same point.

Further, the analysis unit 54 brings the data on distribution of eye refractive power and the data on distribution of corneal radius of curvature into two-dimensional correspondence with each other in order to obtain an ablation amount (an amount of cornea to be ablated) in corneal surgery. Brief description thereof will be given hereinafter.

First, the analysis unit 54 obtains three-dimensional data on a pre-operative corneal shape from the data on distribution of pre-operative corneal radius of curvature obtained by the corneal shape measurement, and then convert it into data on distribution of pre-operative corneal refractive power using Snell's law. Next, the analysis unit 54 converts the data on distribution of pre-operative eye refractive power obtained by the eye refractive power measurement into distribution of pre-operative eye refractive power at corneal center. Using the data on distribution of pre-operative corneal refractive power and the data on distribution of pre-operative eye refractive power, the analysis unit 54 obtains refractive power in terms of a corneal refractive power that is required to make the eye E emmetropic. This is referred to as "equivalent emmetropic corneal refractive power" in this specification, and calculated in the following expression:

equivalent emmetropic corneal refractive power=corneal refractive power+eye refractive power The analysis unit 54 further converts data on distribution of the equivalent emmetropic corneal refractive power into data on distribution of post-operative corneal radius of curvature, in other words into three-dimensional data on a post-operative corneal shape, using Snell's law. Finally, the analysis unit 54 subtracts the thus obtained three-dimensional data on the post-operative corneal shape from the three-dimensional data on the pre-operative corneal shape to calculate the ablation amount. The obtained data on distribution of the equivalent emmetropic corneal refractive power is also displayed in a color map as show in FIG. 7, while the ablation amount is graphically displayed in three-dimensions in a bird's eye view and the like (See U.S. Pat. No. 6,033,075 for the details.)

The thus obtained data on ablation amount is outputted to a corneal surgery apparatus 90 via a communication port 59b or a floppy disk 59c inserted in a floppy disk drive 59a and used in corneal surgery (refractive surgery).

As described above, data on distribution of corneal radius of curvature and data on distribution of eye refractive power, which are measured at different times are aligned their two-dimensional positions before calculating new data such as data on distribution of equivalent emmetropic corneal refractive power or an ablation amount from both the data on distribution so that accurate results are obtained.

Further, in the above embodiment, deviation in the X and Y directions between the data on distribution of corneal radius of curvature and the data on distribution of eye refractive power is corrected with reference to the position of the image of the alignment target (corneal center). Yet, it is also possible to obtain the pupillary center using the image of the anterior eye segment photographed at the time of each measurement in order to use the thus obtained pupillary center as a reference position for two-dimensional alignment. To obtain the pupillary center, for example, the photographed image is subjected to image processing to divide the image into sections with a vertical line and a horizontal line, intersection points of each line and pupillary edge are connected with line segments, and finally the intersection point of the perpendicular bisectors of each line segment is determined as the pupillary center. An alternative to obtain the pupillary center is that the pupillary edge is obtained through image processing and the barycenter of the inner area enclosed with the edge is determined as the pupillary center. Further, the corneal center or the pupillary center may be designated by clicking the mouse 57 on each image of the anterior eye segment displayed on the monitor 39, then the deviation in the X and Y directions may be corrected with reference to the designated point.

Up to this point, description has been given to the case where plural measurement data are aligned with each other in a manner to correct the deviation in the X and Y directions. In addition, if there is an angular deviation between the measurement data in their rotation angles (the inclination angles) of the eye, it is preferred to the angular deviation is also corrected to align the rotation angles. The rotation angles are aligned with each other, for example, in the following manner.

FIG. 9 is an example of the screen of the monitor 39 simultaneously displaying an image 70 of the anterior eye segment photographed at the time of the eye refractive power measurement and an image 75 of the anterior eye segment photographed at the time of the corneal shape measurement. Each image has been stored in the memory 43 at the time of each measurement. In this example, description is given provided that the alignment in the X and Y directions is performed with reference to the corneal center in both measurements, and that the eye E (the head) is inclined at the time of the eye refractive power measurement as compared with the time of the corneal shape measurement.

The examiner observes the images 70 and 75 of the anterior eye segment to find specific points that are common to both images through close observation of the iris pattern. In the image 70 of the anterior eye segment, the examiner clicks the mouse 57 on two specific points 71 and 72 in order to draw a line segment 73 connecting them. Similarly, in the image 75 of the anterior eye segment onto with the ring pattern is projected, the examiner clicks the mouse 57 on specific points 76 and 77 that correspond to the specific points found in the images 70 of the anterior eye segment, to draw a line segment 78 connecting them. The alignment deviation between their rotation angles of the eye E at the time of the two measurements may be determined from the line segments 73 and 78. In this way, the calculation unit 51 which determines the alignment state obtains the amount of angular deviation in the rotation angles. When displaying the map 64a indicating the distribution of eye refractive power and the map 64b indicating the distribution of corneal radius of curvature, as in FIGS. 7 and 8 which are previously shown, the control unit 56 controls the display in a manner to correct the angular deviation between the rotation angles so as to align the maps with each other.

Further, before calculation the distribution of the equivalent emmetropic corneal refractive power or the ablation amount, the analysis unit 54 corrects the angular deviation between the rotation angles. The calculation is carried out using the data on distribution of eye refractive power and the data on corneal radius of curvature that are aligned with each other.

In this embodiment, the specific points are determined by the iris pattern. Yet, the specific points may be the points that are determined by a position of a cilia or by a shadow of a nose, or alternatively, the specific points may be extracted automatically by the apparatus through image processing.

(II) Analysis of Accommodative power of Crystalline Lens

Next, description is given to the case where eye refractive power at far vision and eye refractive power at near vision are measured, and both the measurement data are analyzed to obtain the accommodative power of crystalline lens.

A far/near eye refractive power measurement mode is selected at a push of the switch 40. First, in a similar manner to the corneal ablation amount analysis, distribution of eye refractive power at far vision is measured by the eye refractive power measurement optical system 120. In this case, since the measurement is performed using the fogging technique, obtained data on distribution of eye refractive power is the data on distribution at far vision where the accommodation of the eye is relaxed. Further, an alignment state at the time of measurement is dealt with similarly to the above. That is, the calculation unit 51 obtains information on alignment deviation by detecting the image of the alignment target, and then the memory unit 45 stores the thus obtained information together with the measurement results.

Next, the calculation and control unit 50 moves the lens 28 to a position where the fixation point on the fixation target plate 29 forms an image at a predetermined near distance so that distribution of eye refractive power is measured under the accommodative load applied to the eye E. For example, if the previously measured SE value (spherical equivalent value) of the eye refractive power at far vision is −3 D (diopters), the lens 28 needs to be moved in such a manner to place the fixation point forms an image at −3 D−2.5 D=−5.5 D so that the eye E is fixated at a near distance of 40 cm.

In the case where accommodative load is applied to the eye E, the pupil tends to contract. As a result, the alignment may not be performed with reference to the corneal center. If such is the case, the alignment at the time of eye refractive power measurement at near vision is performed with reference to the pupillary center following the aforementioned example. The calculation unit 51 obtains information on alignment deviation at that time, and the memory unit 45 stores the thus obtained information together with the measurement results.

An accommodative power analysis unit 55 obtains distribution of difference between the data on distribution of eye refractive power at far vision and the data on distribution of eye refractive power at near vision. An eye focuses on an object at far or at near by changing the thickness of the crystalline lens. Accordingly, change in the refractive power of the crystalline lens is obtained from the difference in the distribution of eye refractive power between far vision and near vision, and the obtained results may be used for evaluating or diagnosing accommodative power of the eye. Here, the analysis unit 55 aligns each data on distribution to adjust the positional relationship between them based on the information on the alignment deviation. As a result, two-dimensional deviation from each other is eliminated and hence accurate data is obtained. Further, if the rotation angles of the eye differ in both the measurement, the angular deviation is corrected in the afore-mentioned manner.

Similarly to the above example, the data on distribution of eye refractive power at far vision, the data on distribution of eye refractive power at near vision, and the data on distribution of diffidence are displayed in a form of a color map on the monitor 39. Also in this case, each map is displayed with its center made to coincide with the corneal center being the alignment reference, and with the rotation angle corrected. Such display helps to make accurate comparisons of the distribution of eye refractive power shown in each map.

In the eye refractive power measurement in the embodiment described above, description is given to the example where alignment is performed with reference to the pupillary center. Yet, even in the case alignment is performed with reference to the corneal center, usually, there still exists an error in some degree. Accordingly, if each measurement data is two-dimensionally aligned with the other, analyses and the like using the data are carried out more accurately.

Further, in the embodiment described above, the two measurement mechanisms, one for the corneal shape measurement and the other for eye refractive power measurement, are contained in one apparatus. Instead of this example, the two mechanisms may be constructed as two separate apparatuses. For example, measurement data and alignment information obtained by a corneal shape measurement apparatus and those obtained by an eye refractive power measurement apparatus are inputted to an external computer. The two measurement data are aligned in the external computer and then displayed or used for calculation.

Still further, in addition to the data on distribution of eye refractive power, the data on distribution of corneal radius of curvature and the like, data on distribution of corneal thickness is one of the data that require two-dimensional alignment. The corneal thickness measurement is carried out in the following manner. First, slit light is made to enter the cornea from an oblique direction, a cross-sectional image of the cornea that is optically cut by the slit light is successively photographed from the front, and then the curves of anterior and posterior surfaces of the cornea are obtained from the photographed images. Using the detected curves of anterior and posterior surfaces of the cornea, the thickness of the cornea at an intended point is calculated. By repeating the calculation to obtain the thickness over the whole cornea, distribution of the corneal thickness is obtained. Alternatively, while slit light is made to enter the cornea from the front and to rotate about the corneal center, the cross sectional image that is optically cut with the slit light is successively photographed by a camera disposed in an oblique direction from the cornea in accordance with the Scheimplug principle. Distribution of the corneal thickness is obtained through analyzing the photographed images.

By analyzing the thus obtained data on distribution of corneal thickness through comparison with the two-dimensional data on ablation amount which is obtained in the afore-mentioned embodiment, it is possible to determine whether or not the ablation amount is suitable to the examinee in view of the corneal thickness. In this case, also, the data need to be aligned two-dimensionally with each other based on the alignment state at the time of each measurement in order to carry out comparison and analysis of the data.

As described above, according to the present invention, measurement data measured at different times are two-dimensionally aligned with each other so that each data is compared or analyzed accurately and easily.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic apparatus comprising:

a first input unit with which plural measurement data concerning an eye to be examined are inputted, each of the measurement data having a different characteristic;

a second input unit with which images of the eye including an anterior eye segment are inputted, each of the images being photographed at the time of measuring each of the inputted measurement data; and a calculation and control unit which obtains a common reference point based on the inputted images, obtains two-dimensional displacement or deviation between each of the measurement data based on the obtained common reference point, and performs two-dimensional data matching of each of the measurement data.

2. The ophthalmic apparatus according to claim 1, further comprising a display, and wherein the calculation and control unit obtains new data by performing the two-dimensional data matching of each of the measurement data and graphically displays on the display the thus obtained data.

3. The ophthalmic apparatus according to claim 1, further comprising a display, and wherein the calculation and control unit graphically displays on the display each of the measurement data using the common reference point.

4. The ophthalmic apparatus according to claim 1, wherein the calculation and control unit obtains the displacement or deviation between each of the measurement data with reference to a corneal center or a pupillary center in each of the inputted images as the common reference point.

5. The ophthalmic apparatus according to claim 1, wherein the calculation and control unit obtains the displacement or deviation between each of the measurement data with reference to specific points that are commonly found in each of the inputted images as the common reference point.

6. The ophthalmic apparatus according to claim 1, further comprising a display, and wherein the calculation and control unit displays each of the inputted images on the display, and obtains the displacement or deviation between each of the measurement data using each of designated points on each of the displayed images as the common reference point.

7. The ophthalmic apparatus according to claim 1, wherein the first input unit inputs data on distribution of pre-operative corneal radius of curvature of the eye and data on distribution of pre-operative eye refractive power of the eye, and the calculation and control unit obtains the displacement or deviation between each of the data on distribution, and obtains data on distribution of equivalent emmetropic corneal refractive power, which is refractive power required for the eye to be emmetropic expressed in terms of corneal refractive power, by performing the two-dimensional data matching of each of the data on distribution.

8. The ophthalmic apparatus according to claim 1, wherein the first input unit inputs three-dimensional data on a pre-operative corneal shape of the eye and three-dimensional data on a post-operative corneal shape of the eye, and the calculation and control unit obtains the displacement or deviation between each of the three-dimensional data, and obtains data on an ablation amount of cornea by performing the two-dimensional data matching of each of the three-dimensional data.

9. The ophthalmic apparatus according to claim 1, wherein the first input unit inputs data on distribution of eye refractive power of the eye at far vision and data on distribution of eye refractive power of the eye at near vision, and the calculation and control unit obtains the displacement or deviation between each of the data on distribution, and obtains data on distribution of difference between the two data on distribution by performing the two-dimensional data matching of each of the data on distribution.

10. The ophthalmic apparatus according to claim 1, further comprising a display, and wherein the first input unit inputs data on distribution of corneal thickness of the eye and data on an ablation amount of the cornea, and the calculation and control unit obtains the displacement or deviation between each of the data, and displays on the display results of comparison between each of the data by performing the two-dimensional data matching of each of the data.

11. The ophthalmic apparatus according to claim 1, further comprising:

a corneal shape measurement unit which measures distribution of corneal radius of curvature of the eye, the corneal shape measurement unit having
an optical system for projecting a first measurement target onto the cornea of the eye, and
an optical system for detecting an image of the first measurement target formed on the cornea; and an eye refractive power measurement unit which measures distribution of eye refractive power of the eye, the eye refractive power measurement unit having
an optical system for projecting a second measurement target onto a fundus of the eye, and
an optical system for detecting an image of the second measurement target formed on the fundus, and wherein the first input unit inputs data on the measured distribution of corneal radius of curvature and data on the measured distribution of eye refractive power to the calculation and control unit.

12. The ophthalmic apparatus according to claim 11, further comprising an alignment unit which detects an alignment state of the ophthalmic apparatus relative to the eye, the alignment unit having
an optical system for projecting an alignment target onto a cornea of the eye, and
an optical system for detecting an image of the alignment target formed on the cornea, and
wherein the calculation and control unit obtains the displacement or deviation between each of the inputted data on distribution with reference to a position of the image of the alignment target detected at the time of each measurement as the common reference point.

13. An ophthalmic apparatus comprising:

a corneal shape measurement unit which measures distribution of corneal radius of curvature of an eye to be examined, the corneal shape measurement unit having
an optical system for projecting a first measurement target onto a cornea of the eye, and
an optical system provided with a first photographing element for detecting an image of the first measurement target formed on the cornea;

an eye refractive power measurement unit which measures distribution of eye refractive power of the eye, the eye refractive power measurement unit having
an optical system for projecting a second measurement target onto a fundus of the eye, and
an optical system for detecting an image of the second measurement target formed on the fundus;

an alignment unit which detects an alignment state of the ophthalmic apparatus relative to the eye, the alignment unit having
an optical system for projecting an alignment target onto the cornea of the eye, and
an optical system provided with a second photographing element for photographing an image of the alignment target formed on the cornea; and a calculation and control unit which detects and corrects two-dimensional displacement or deviation between each of data on the measured distribution with reference to at least an image of the eye including an anterior eye segment photographed by either the first photographing element or the second photographing element at the time of each measurement.

14. An ophthalmic apparatus comprising:

a first input unit with which first measurement data concerning an eye to be examined is inputted, the first measurement data being obtained with reference to a two-dimensional reference point;

a second input unit with which second measurement data concerning the eye is inputted together with two-dimensional alignment displacement or deviation of the eye relative to the reference point obtained by detecting an alignment state of the eye at the time of measuring the inputted second measurement data; and a calculation and control unit which performs two-dimensional data matching of each of the measurement data based on the reference point.

15. An ophthalmic apparatus in which data are exchanged between at least two ophthalmic devices comprising:

a first ophthalmic device photographing an eye to be examined including its anterior eye segment at the time of a measurement and storing a photographed image of the eye;

a second ophthalmic device photographing the eye to be examined, including its anterior eye segment, identical to the eye photographed by the first ophthalmic device;

a calculation unit which finds a common part to the images of the eye photographed by the first and the second ophthalmic devices and detects a two-dimensional displacement or deviation between the photographed images; and correcting means for correcting the data exchanged between the first and second ophthalmic devices based on the detected displacement or deviation.

* * * * *

UNITED STATES PATENT AND TRADEMARK OFFICE
CERTIFICATE OF CORRECTION

PATENT NO. : 6,655,805 B2 Page 1 of 1
DATED : December 2, 2003
INVENTOR(S) : Masanao Fujieda It is certified that error appears in the above-identified patent and that said Letters Patent is hereby corrected as shown below:

<u>Title page,</u>
Item [56], References Cited, please add the following:
-- U.S. PATENT DOCUMENTS
5,500,697     3/1996      Fujieda
5,841,511     11/1998     D'Souza et al.
5,907,388     5/1999      Fujieda
6,033,075     3/2000      Fujieda et al.

FOREIGN PATENT DOCUMENTS
EPO   0811352     10/1997
JP     03-188826   08/1997
JP     08-103413   4/1996 --.

Signed and Sealed this

Thirtieth Day of March, 2004

JON W. DUDAS
*Acting Director of the United States Patent and Trademark Office*